(12) United States Patent
Kusterbeck

(10) Patent No.: US 7,813,938 B2
(45) Date of Patent: Oct. 12, 2010

(54) METHOD AND SYSTEM FOR PRESCRIPTION DISTRIBUTION SECURITY

(76) Inventor: Shawn Kusterbeck, 3 Aviary St., Warrenton, VA (US) 20186

( * ) Notice: Subject to any disclaimer, the term of this patent is extended or adjusted under 35 U.S.C. 154(b) by 1302 days.

(21) Appl. No.: 10/417,125

(22) Filed: Apr. 17, 2003

(65) Prior Publication Data

US 2003/0197366 A1 Oct. 23, 2003

Related U.S. Application Data

(60) Provisional application No. 60/372,810, filed on Apr. 17, 2002.

(51) Int. Cl.
*G06Q 10/00* (2006.01)
(52) U.S. Cl. ............... 705/2; 705/3; 235/375; 235/462.15; 283/69
(58) Field of Classification Search ........... 705/2–3; 235/375, 380, 462, 462.15; 382/115; 283/69
See application file for complete search history.

(56) References Cited

U.S. PATENT DOCUMENTS

| 5,883,370 | A | * | 3/1999 | Walker et al. | 235/375 |
|---|---|---|---|---|---|
| 6,030,581 | A | * | 2/2000 | Virtanen | 422/68.1 |
| 6,219,439 | B1 | * | 4/2001 | Burger | 382/115 |
| 6,421,650 | B1 | * | 7/2002 | Goetz et al. | 705/3 |
| 2002/0035484 | A1 | * | 3/2002 | McCormick | 705/2 |
| 2002/0112164 | A1 | * | 8/2002 | Schmeling et al. | 713/176 |
| 2003/0074225 | A1 | * | 4/2003 | Borsand et al. | 705/3 |
| 2003/0167190 | A1 | * | 9/2003 | Rincavage et al. | 705/3 |
| 2003/0195774 | A1 | * | 10/2003 | Abbo | 705/3 |
| 2005/0182656 | A1 | * | 8/2005 | Morey | 705/2 |

* cited by examiner

*Primary Examiner*—Vanel Frenel
(74) *Attorney, Agent, or Firm*—Bradford Kile; Kile Goekjian Reed & McManus

(57) ABSTRACT

A method and system for enhanced prescription distribution security wherein a prescription form is provided with one or more of: (1) a bar code corresponding to a data base location for a physician's signature; (2) a bar code corresponding to the pharmaceutical/medication to be dispensed and (3) a bar code unique to each prescription form.

5 Claims, 2 Drawing Sheets

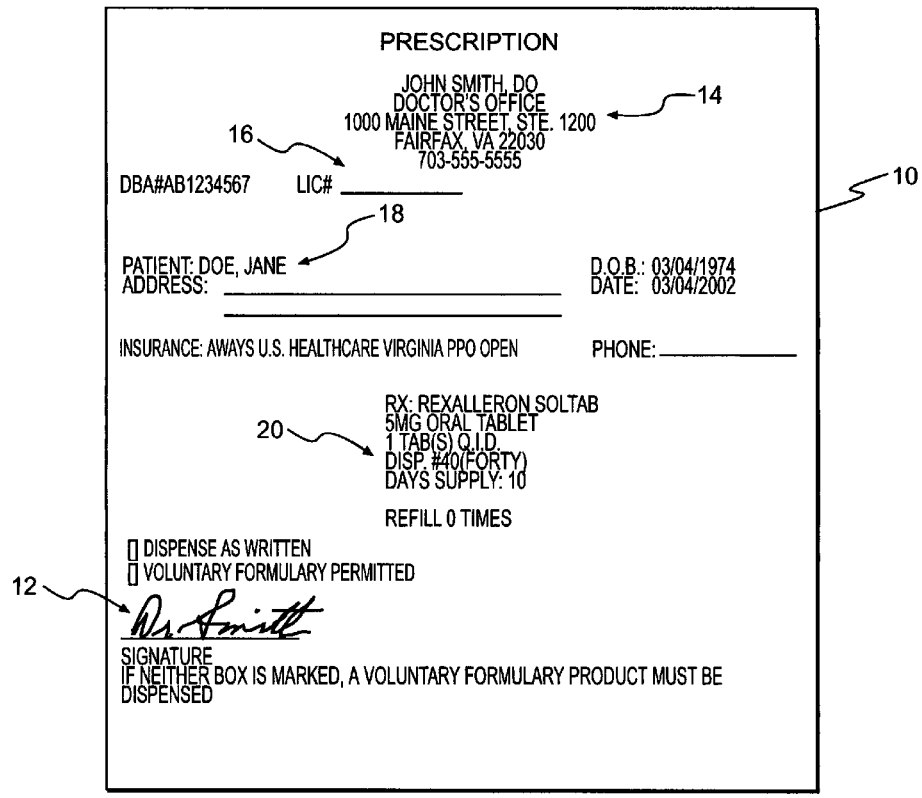

FIG. 1

PRESCRIPTION

JOHN SMITH, DO
DOCTOR'S OFFICE
1000 MAINE STREET, STE. 1200
FAIRFAX, VA 22030
703-555-5555

DBA#AB1234567   LIC#_____

PATIENT: DOE, JANE
ADDRESS: _____

D.O.B.: 03/04/1974
DATE:  03/04/2002
PHONE: _____

INSURANCE: AWAYS U.S. HEALTHCARE VIRGINIA PPO OPEN

RX: REXALLERON SOLTAB
5MG ORAL TABLET
1 TAB(S) Q.I.D.
DISP #40(FORTY)
DAY'S SUPPLY: 10

REFILL 0 TIMES

☐ DISPENSE AS WRITTEN
☐ VOLUNTARY FORMULARY PERMITTED

SIGNATURE
IF NEITHER BOX IS MARKED, A VOLUNTARY FORMULARY PRODUCT MUST BE DISPENSED

FIG. 2

METHOD AND SYSTEM FOR PRESCRIPTION DISTRIBUTION SECURITY

RELATED PROVISIONAL APPLICATION

This application claims the benefit of U.S. Provisional Application No. 60/372,810 entitled "Method and System for Prescription Distribution Security" filed on Apr. 17, 2002. The Provisional Application is of common inventorship with the subject application.

BACKGROUND OF THE INVENTION

Field of the Invention

The present invention relates to a method and system to track prescriptions and provide lawful distribution with enhanced security and safety. More specifically, the invention is directed at providing a system that allows pharmacists and/or pharmacies to better monitor a patient's prescription information avoiding fraud, unauthorized copying and errors.

The lawful distribution of pharmaceuticals in the United States is a two step process. Initially an attending physician prescribes a pharmaceutical or drug for treatment of a patient's condition or symptom(s). Secondly the prescription is transmitted to a pharmacist or pharmacy to have the prescription filled and sold to a patient. Although each step in the process is subject to good faith error, and thus will admit to worthwhile improvement just to be more accurate, a significant concern involves the introduction of the possibility for fraud in the distribution of controlled substances. In this, false or fake prescriptions can be delivered to a pharmacy and filled when there was no lawful basis to release the controlled substance for distribution. Although various electronic systems have been envisioned to create more accurate database information and eliminate errors produced by a physician's handwriting, such electronic systems are still subject to willful fraud. The subject invention is envisioned to assist in the reduction of honest errors in the drug distribution process and more significantly to ameliorate actual fraud in the distribution system.

The subject invention is designed to utilize: (1) signature barcodes, (2) drug barcodes and (3) prescription serial numbers alone or in any combination to address this problem of fraud in the legal drug industry.

OBJECTS OF THE INVENTION

It is, therefore, a general object of the invention to provide a method and system for pharmaceutical distribution with enhanced accuracy and security.

It is another general object of the invention to provide a method and system for pharmaceutical distribution where errors in filling a prescription can be reliably minimized.

It is another general object of the invention to provide a method and system for pharmaceutical distribution wherein the potential for fraud and theft can be minimized.

SUMMARY OF THE INVENTION

The subject method and system that is intended to accomplish at least some of the foregoing objects comprises a prescription system that included use of bar code information for any one or a combination of: (1) physician signature verification, (2) medication verification bar code information and/or (3) serial number information that is applied to individual prescription that can be read monitored and verified by a distributing pharmacist before a prescription is filled and sold.

DRAWINGS

Other objects and advantages of the present invention will become apparent from the following detailed description of preferred embodiments thereof taken in conjunction with the accompanying drawings, wherein:

FIG. 1 is a view of a standard pharmaceutical prescription form as currently used in the pharmaceutical field to fill prescriptions; and FIG. 2 is a view of a prescription form containing a signature bar code, a medicine bar code and a serial number bar code in accordance with the invention.

DETAILED DESCRIPTION

Turning now to the drawings wherein like references refer to like parts, FIG. 1 discloses a standard prescription form that is used by physicians to write prescriptions. The form 10 typically includes a signature line 12 for a prescribing health care provider and numerous other details such as the physician's office address 14, his license number 16, and patient's name 18 and address and telephone number and a description of the drug to be filled 20.

In the subject invention the prescription form is also provided with one or more security and information verification means in the form of bar coded data.

Signature Barcode

In a preferred embodiment a barcode 22, note FIG. 2, will be placed just to the right of the doctor's signature. Pharmacists will be able to scan the barcode, which will bring up three samples of the doctor's signature on their computer screens. The signatures will be samples taken from the doctor at three different times of the day (morning, noon, and the late afternoon), since doctor's signatures to a data base firm which will scan them and put them into a database which is accessible by a participating pharmacy directly on site via a computer disc or online via the Internet. The pharmacists will be able to see a sample of any doctor's signature, throughout the United States. The signature barcode will:

Help pharmacists verify prescriptions from doctors, whose signatures they are not familiar with.

Show pharmacists the variations in doctor's signatures that occur throughout the day. Doctor's signatures commonly look differently depending on many factors; time of day, how busy the doctor was when he wrote the script, how the doctor was feeling that day, how many prescription he has written, etc.

Barcode data will also be an element that makes forging a prescription more difficult. If the forger is unable to acquire the signature barcode, they will be unable to write a false prescription.

Pharmacists will be able to match the barcode, with the doctor's signature. If they scan the barcode and a different doctor's name comes up on their screen, then the prescription request is fraudulent.

Pharmaceutical/Medication Bar Code

A medicine barcode 24 will help to insure accuracy and verify forged prescriptions. Pharmacists will now be able to:

Scan the medicine barcode, instead of introducing a risk of making an error while entering it by hand.

Match the barcode to the pharmaceutical/medication which has a manufacturer's bar code associated with the container which is another defense against forgery.

Scanning a barcode will save time and effort for the pharmacists, limiting their mistakes and insuring accuracy. They will also be able to spot a fake prescriptions instantly, if the barcode does not match the pharmaceutical/medication for which it is written.

Serial Number Bar Code

All prescription will preferably be assigned a distinct serial number 26. The serial number will:

Guard against someone copying a prescription. Prescription numbers will only be able to be filled once, so if someone tries to fill a number which has already been filled, the pharmacists will appreciate that it is a copy.

Pharmacists will be able to track a prescription better. Doctors will know which numbers go with prescriptions, so if a pharmacists calls and asks a doctor what medicine and to whom he prescribed prescription number 210456, the doctor will be able to verify this prescription more accurately.

Summary of Major Advantages of the Invention

After reading and understanding the foregoing description of the invention, in conjunction with the illustrative drawings, it will be appreciated that several advantages of the subject method and system for prescription distribution security are obtained.

One advantage of the present invention is that it helps pharmacists verify prescriptions from doctors, whose signatures they are not familiar with by showing pharmacists the variations in doctor's signatures that occur throughout the day.

Another advantage of the present invention is that it avoids fraudulent prescriptions by guarding against someone copying a prescription. Yet another advantage of the present invention is that pharmacists will be able to track the prescription better. Pharmacists will be able to use the serial number to verify when and where the prescription was filled before, in case of someone duplicating the script.

A further advantage of the present invention is that it prevents mistakes in the dispensing of legal pharmaceuticals and medication.

In describing the invention, reference has been made to a preferred embodiment and illustrative advantages of the invention. Those of skill in the art, however, and familiar with the instant disclosure of the subject invention may recognize additions, deletions, modifications, substitutions and other changes which will fall within the purview of the subject invention set forth in the following claims.

What is claimed is:

1. A method for enhancing the security of prescription distribution comprising the steps of:

providing a physician with a physician prescription form to receive the physician's prescription information and the physician's signature;

adding to the prescription form a bar code that corresponds to previously recorded instances of the physician's signature within a computer readable data base;

comparing the physician's signature on the physician prescription form with the previously recorded instances of the physician's signature contained within the computer readable data base, said comparison occurring at a location of prescription distribution for a match before a prescription is filled; and wherein said previously recorded instances of the physician's signature within the data base comprise a plurality of samples of the physician's signature recorded at different times of the day.

2. A method for enhancing the security of prescription distribution as defined in claim 1 and further comprising the step of:

adding a pharmaceutical/medication bar code to said prescription form that corresponds to the pharmaceutical/medication prescribed by the physician.

3. A method for enhancing the security of prescription distribution as defined in claim 2 and further comprising the step of:

adding a unique numerical bar code to the prescription form.

4. A method for enhancing the security of prescription distribution comprising the steps of:

providing an authorized person with a prescription form to receive prescription information and the authorized person's signature;

adding to the prescription form a bar code that corresponds to previously recorded instances of the authorized person's signature within a computer readable data base;

comparing the authorized person's signature on the prescription form with the previously recorded instances of the authorized person's signature contained within the computer readable data base, said comparison occurring at a location of prescription distribution for a match before a prescription is filled; and wherein said comparing comprises comparing the authorized person's signature on the prescription form with a plurality of previously recorded instances of the authorized person's signature within the computer readable database.

5. A method for enhancing the security of prescription distribution as defined in claim 4, wherein:

said previously recorded instances of the authorized person's signature within the computer readable data base comprise a plurality of samples of the authorized person's signature recorded at different times of the day.

* * * * *